United States Patent
Zhan et al.

(10) Patent No.: US 10,460,508 B2
(45) Date of Patent: Oct. 29, 2019

(54) VISUALIZATION WITH ANATOMICAL INTELLIGENCE

(71) Applicant: Siemens Healthcare GmbH, Erlangen (DE)

(72) Inventors: Yiqiang Zhan, Berwyn, PA (US); Gerardo Hermosillo-Valadez, West Chester, PA (US); Xiang Sean Zhou, Exton, PA (US); Matthias Fenchel, Erlangen (DE); Berthold Kiefer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 146 days.

(21) Appl. No.: 14/735,243

(22) Filed: Jun. 10, 2015

(65) Prior Publication Data
US 2015/0363963 A1 Dec. 17, 2015

Related U.S. Application Data

(60) Provisional application No. 62/011,273, filed on Jun. 12, 2014.

(51) Int. Cl.
*G06T 15/08* (2011.01)
*A61B 5/055* (2006.01)
(Continued)

(52) U.S. Cl.
CPC ............. *G06T 15/08* (2013.01); *A61B 5/0033* (2013.01); *A61B 5/055* (2013.01); *G06K 9/4671* (2013.01);
(Continued)

(58) Field of Classification Search
CPC ....... G06T 7/00; G06T 2207/00; G06T 15/08; G06T 7/149; G06T 7/11; G06T 19/20;
(Continued)

(56) References Cited

U.S. PATENT DOCUMENTS

| | | | | |
|---|---|---|---|---|
| 6,201,543 B1 * | 3/2001 | O'Donnell | ........... | G06K 9/6207 345/420 |
| 7,835,497 B2 * | 11/2010 | Haras | .................. | A61B 5/1075 378/98 |

(Continued)

FOREIGN PATENT DOCUMENTS

CN 102648482 A 8/2012

OTHER PUBLICATIONS

Twining, Carole J., Stephen Marsland, and Christopher J. Taylor. "Measuring Geodesic Distances on the Space of Bounded Diffeomorphisms." BMVC. vol. 2. 2002.*
(Continued)

*Primary Examiner* — Luther Behringer
*Assistant Examiner* — Sean D Mattson

(57) ABSTRACT

A framework for facilitating visualization, including localizing at least one anatomical structure of interest in image data. The structure of interest is then highlighted by reformatting the image data by mapping landmarks associated with the structure of interest to corresponding points along a contour of a geometric shape and warping the image data based on the mapped landmarks. The resulting reformatted image data is rendered for display to a user.

10 Claims, 6 Drawing Sheets

(51) Int. Cl.
   *G06T 19/20*   (2011.01)
   *G06T 7/11*    (2017.01)
   *G06T 7/149*   (2017.01)
   *G06K 9/46*    (2006.01)
   *A61B 5/00*    (2006.01)
(52) U.S. Cl.
   CPC .............. *G06T 7/11* (2017.01); *G06T 7/149* (2017.01); *G06T 19/20* (2013.01); *A61B 5/4504* (2013.01); *G06T 2207/10088* (2013.01); *G06T 2207/20128* (2013.01); *G06T 2210/41* (2013.01); *G06T 2219/008* (2013.01)
(58) Field of Classification Search
   CPC ..... G06T 2219/008; G06T 2219/20128; G06T 2219/10088; G06T 2219/41; G06K 9/00; G06K 9/4671; A61B 5/00; A61B 5/0033; A61B 5/055; A61B 5/4504
   See application file for complete search history.

(56) References Cited

U.S. PATENT DOCUMENTS

| | | | | |
|---|---|---|---|---|
| 2002/0127523 | A1* | 9/2002 | Edic | G06T 11/006 434/211 |
| 2004/0122309 | A1* | 6/2004 | Deller | G06T 15/08 600/425 |
| 2007/0047790 | A1* | 3/2007 | Dewaele | G06K 9/4671 382/128 |
| 2007/0081706 | A1* | 4/2007 | Zhou | G06F 19/321 382/128 |
| 2007/0081712 | A1* | 4/2007 | Huang | G06T 7/33 382/128 |
| 2007/0249910 | A1* | 10/2007 | Kiraly | G06T 7/60 600/300 |
| 2008/0044074 | A1* | 2/2008 | Jerebko | G06T 7/149 382/128 |
| 2008/0049991 | A1* | 2/2008 | Gering | G06T 19/00 382/128 |
| 2008/0049999 | A1* | 2/2008 | Jerebko | G06T 7/0012 382/128 |
| 2008/0107318 | A1* | 5/2008 | Kiraly | G06T 17/00 382/131 |
| 2008/0287796 | A1* | 11/2008 | Kiraly | A61B 5/103 600/443 |
| 2009/0136103 | A1* | 5/2009 | Sonka | G06K 9/4638 382/128 |
| 2010/0128954 | A1* | 5/2010 | Ostrovsky-Berman | G06T 7/187 382/131 |
| 2012/0172700 | A1* | 7/2012 | Krishnan | A61B 6/032 600/407 |
| 2013/0070996 | A1* | 3/2013 | Liu | G06K 9/00 382/131 |
| 2013/0094704 | A1* | 4/2013 | Hamadeh | G06T 7/136 382/103 |
| 2015/0262387 | A1 | 9/2015 | Zebaze et al. | |

OTHER PUBLICATIONS

Keiper, M. D., R. A. Zimmerman, and L. T. Bilaniuk. "MRI in the assessment of the supportive soft tissues of the cervical spine in acute trauma in children." Neuroradiology 40.6 (1998): 359-363. (Year: 1998).*

Kreiser, Julian, et al. "A Survey of Flattening-Based Medical Visualization Techniques." Computer Graphics Forum. vol. 37. No. 3. 2018. (Year: 2018).*

Vrtovec, Tomž, et al. "Automated generation of curved planar reformations from MR images of the spine." Physics in Medicine & Biology 52.10 (2007): 2865. (Year: 2007).*

Office action dated Oct. 19, 2018 in CN application No. 201720854062. 8, 7 pages (English translation attached).

* cited by examiner

VISUALIZATION WITH ANATOMICAL INTELLIGENCE

CROSS-REFERENCE TO RELATED APPLICATION

This application claims the benefit of U.S. provisional application No. 62/011,273 filed on Jun. 12, 2014, the entire contents of which are incorporated herein by reference.

TECHNICAL FIELD

The present disclosure generally relates to diagnostic imaging and, more specifically, to automated or semi-automated systems and methods for facilitating visualization with anatomical intelligence.

BACKGROUND

The field of medical imaging has seen significant advances since the time X-Rays were first used to determine anatomical abnormalities. Medical imaging hardware has progressed from modern machines such as Medical Resonance Imaging (MRI) scanners, Computed Tomographic (CT) scanners, and Positron Emission Tomographic (PET) scanners, to multimodality imaging systems such as PET-CT and PET-MRI systems. Because of large amount of image data generated by such modern medical scanners, there has been and remains a need for developing image processing techniques that can automate some or all of the processes to determine the presence of anatomical abnormalities in scanned medical images.

Digital medical images are constructed using raw image data obtained from a scanner. Digital medical images are typically either a two-dimensional ("2-D") image made of pixel elements or a three-dimensional ("3-D") image made of volume elements ("voxels"). Such 2-D or 3-D images are processed using medical image recognition techniques to determine the presence of anatomical abnormalities such as cysts, tumors, polyps, etc. Given the amount of image data generated by any given image scan, it is preferable that an automatic technique should point out anatomical features in the selected regions of an image to a doctor for further diagnosis of any disease or condition.

Automatic image processing and recognition of structures within a medical image is generally referred to as Computer-Aided Detection (CAD). A CAD system can process medical images and identify anatomical structures including possible abnormalities for further review. Such possible abnormalities are often called candidates and are considered to be generated by the CAD system based on the medical images.

Bone metastases, or metastatic bone disease, is a type of abnormality that is of major clinical concern. Bone metastases is a class of cancer metastases that results from primary tumor invasion to bone. Although bone-originating cancers are rare, bones are common targets for cancer cells to spread and settle. Metastases from primary tumors are the most common malignant carcinoma involving skeletons. Their clinical relevance arises from the fact that they are often painful to the patients, and affect a patient's quality of life due to their impact on the stability and motility of a patient's skeleton. Diagnosing bone metastases is therefore highly relevant for therapy decisions.

Medical imaging techniques provide important clues to diagnose and evaluate the progress of bone metastases. Bone scintigraphy (or scan) is the current standard of care. Bone scintigraphy is a nuclear scanning test to find certain abnormalities in bone. This test is highly sensitive, fast and easy to read. However, it is not very specific, and therefore requires an additional imaging scan.

SUMMARY

The present disclosure relates to a framework for facilitating visualization. In accordance with one aspect, the framework localizes at least one anatomical structure of interest in image data. The structure of interest is then highlighted by reformatting the image data. The resulting reformatted image data is then rendered for display to a user.

In accordance with another aspect, the framework automatically localizes at least one bone structure of interest appearing only in a first number of slices in image data. The image data may be reformatted to generate reformatted image data in which the structure of interest appears only in a second number of slices that is less than the first number of slices. The resulting reformatted image data is then rendered for display to a user for detecting bone metastases.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
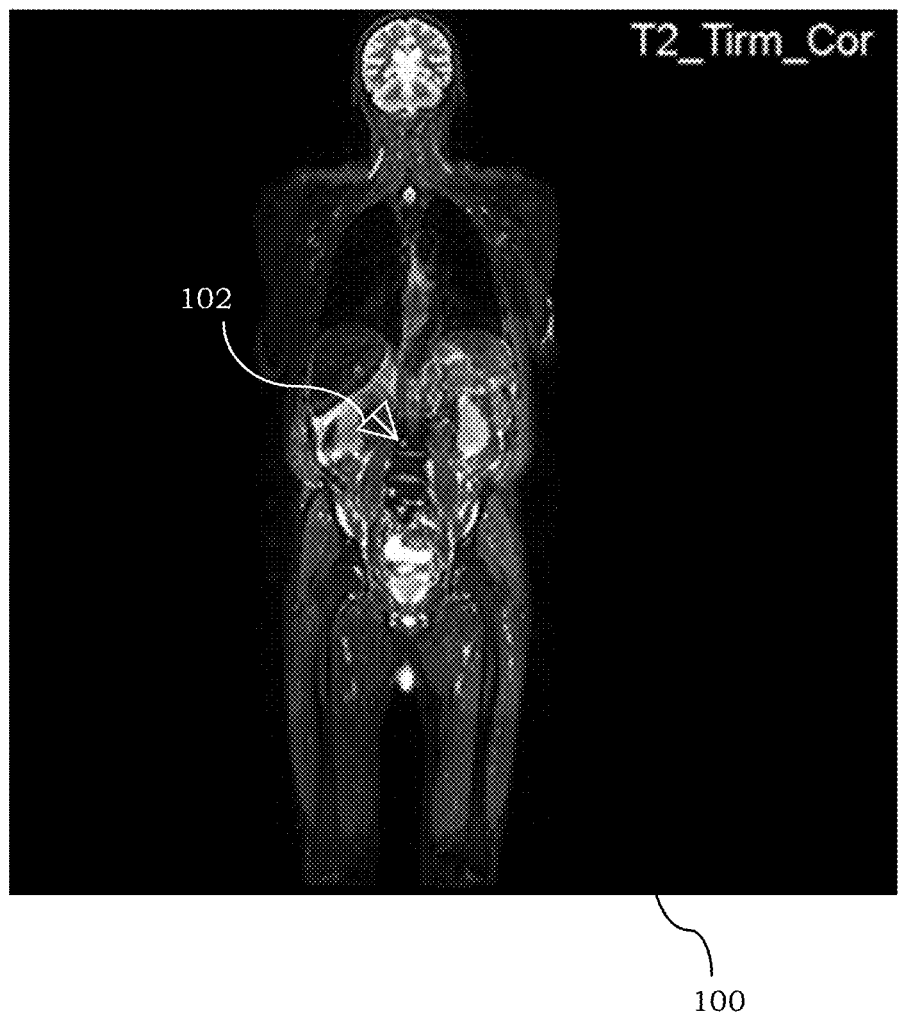
FIG. 1 shows a slice of a T2-weighted coronal magnetic resonance (MR) series.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of a radiosurgery or radiotherapy procedure, which may include times when the radiation source is either on or off. From time to time, for convenience of description, MR imaging data may be used herein as an exemplary imaging modality. It will be appreciated, however, that data from any type of imaging modality including, but not limited to, X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system's memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" refers to multi-dimensional data composed of discrete image elements (e.g., pixels for 2-D images and voxels for 3-D images). The image may be, for example, a medical image of a subject collected by computed tomography, magnetic resonance imaging, ultrasound, or any other medical imaging system known to one of skill in the art. The image may also be provided from non-medical contexts, such as, for example, remote sensing systems, electron microscopy, etc. The methods of the inventions can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of two or three mutually orthogonal axes. The terms "digital" and "digitized" as used herein will refer to images or volumes, as appropriate, in a digital or digitized format acquired via a digital acquisition system or via conversion from an analog image.

Compared to other imaging modalities, whole-body MRI provides high sensitivity and specificity of bone metastasis and a large field of view to cover most of the skeleton. However, it often takes a long time to read the whole-body MR scan data and report all suspicious bone metastases. For example, FIG. 1 shows a slice 100 of a T2-weighted coronal MR series. The triangle 102 indicates the suspicious bone lesion. Although the T2-weighted coronal MR series shows high resolution and sensitivity of bone metastases, it cannot display all vertebrae in one slice due to the curved spine geometry. In order to find all lesions on the vertebrae, a radiologist would need to review more than 15 slices very carefully, which is time consuming and inefficient.

A framework for visualization is described herein. In accordance with one aspect, the framework provides anatomically intelligent visualization to increase the efficiency of reading image data to detect abnormalities, such as bone metastases. To achieve this goal, the image data is processed to highlight the anatomical structure of interest (e.g., bone structure). In some implementations, the image data is processed to display only the structure of interest. Alternatively, the structure of interest may be displayed in fewer number of slices to make reading more efficient. Both types of visualization modes may be built on algorithms that are able to automatically localize the structure of interest in the image data. The framework advantageously provides an efficient and easy way of reading diagnostic images. These exemplary advantages and features will be described in more details in the following description.

Figure 2:
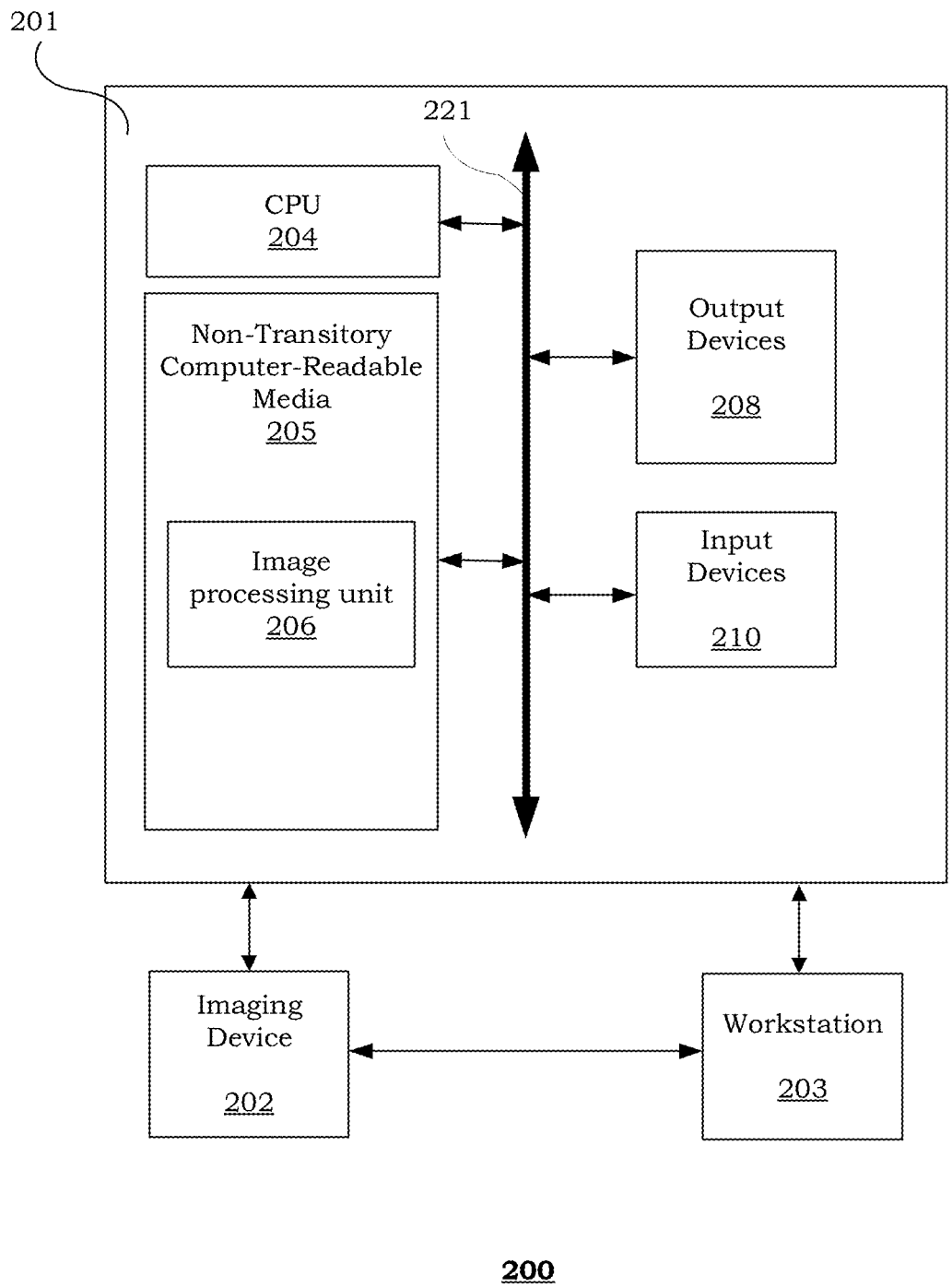
FIG. 2 is a block diagram illustrating an exemplary imaging system.

FIG. 2 is a block diagram illustrating an exemplary imaging system 200. The imaging system 200 includes a computer system 201 for implementing the framework as described herein. The computer system 201 may further be connected to an imaging device 202 and a workstation 203, over a wired or wireless network. The imaging device 202 may be a radiology scanner such as a magnetic resonance (MR) scanner, PET/MR, X-ray or a CT scanner.

Computer system 201 may be a desktop personal computer, a portable laptop computer, another portable device, a mini-computer, a mainframe computer, a server, a storage system, a dedicated digital appliance, or another device having a storage sub-system configured to store a collection of digital data items. In one implementation, computer system 201 comprises a processor or central processing unit (CPU) 204 coupled to one or more non-transitory computer-readable media 205 (e.g., computer storage or memory), output devices 208 (e.g., monitor, display, printer, etc.) and various input devices 210 (e.g., mouse, keyboard, touch pad, voice recognition module, etc.) via an input-output interface 221. Computer system 201 may further include support circuits such as a cache, a power supply, clock circuits and a communications bus. Even further, computer system 201 may be provided with a graphics controller chip, such as a graphics processing unit (GPU) that supports high performance graphics functions.

It is to be understood that the present technology may be implemented in various forms of hardware, software, firmware, special purpose processors, or a combination thereof. In one implementation, the techniques described herein are implemented by image processing unit 206. Image processing unit 206 may include computer-readable program code tangibly embodied in non-transitory computer-readable media 205. Non-transitory computer-readable media 205 may include random access memory (RAM), read only memory (ROM), magnetic floppy disk, flash memory, and other types of memories, or a combination thereof. The computer-readable program code is executed by CPU 204 to control and/or process image data from imaging device 202.

As such, the computer system 201 is a general-purpose computer system that becomes a specific-purpose computer system when executing the computer readable program code. The computer-readable program code is not intended to be limited to any particular programming language and implementation thereof. It will be appreciated that a variety of programming languages and coding thereof may be used to implement the teachings of the disclosure contained herein. Computer system 201 may also include an operating system and microinstruction code. The various techniques described herein may be implemented either as part of the microinstruction code or as part of an application program or software product, or a combination thereof, which is executed via the operating system. Various other peripheral devices, such as additional data storage devices and printing devices, may be connected to the computer system 201.

The workstation 203 may include a computer and appropriate peripherals, such as a keyboard and display, and can be operated in conjunction with the entire system 200. For example, the workstation 203 may communicate with the imaging device 202 so that the image data collected by the imaging device 202 can be rendered at the workstation 203 and viewed on the display. The workstation 203 may include a user interface that allows a radiologist or any other skilled user (e.g., physician, technician, operator, scientist, etc.), to manipulate the image data. For example, a user may identify structures or regions of interest in the image data, or annotate the structures or regions of interest using pre-defined descriptors via the user interface. Further, the workstation 203 may communicate directly with computer system 201 to display processed image data. For example, a radiologist can interactively manipulate the displayed representation of the processed image data and view it from various viewpoints and in various reading modes.

Figure 3:
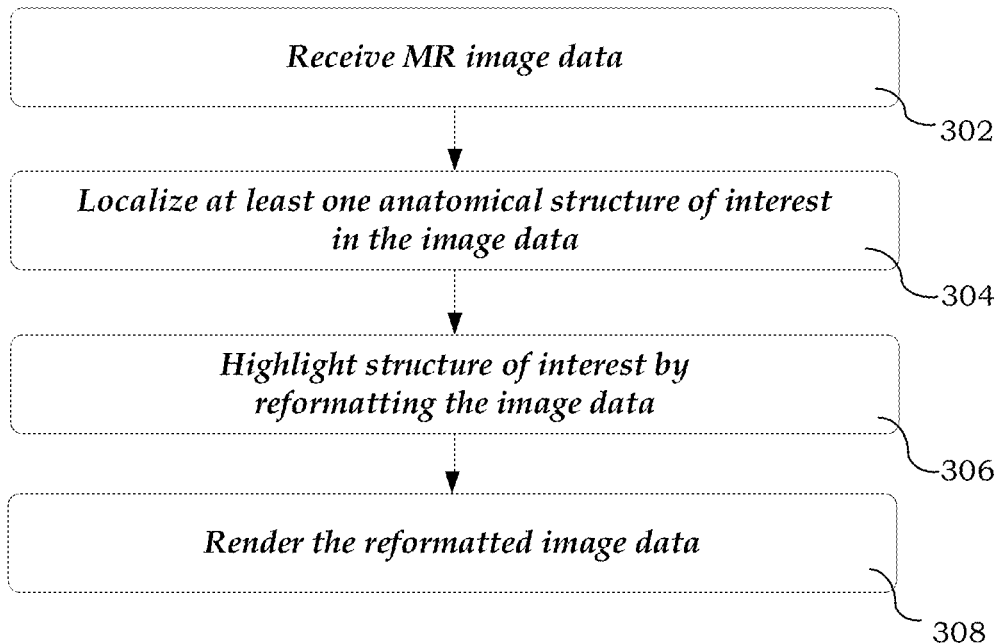
FIG. 3 shows an exemplary visualization method.

FIG. 3 shows an exemplary visualization method 300. It should be noted that the steps of the method 300 may be performed in the order shown or a different order. Furthermore, different, additional or fewer steps may be implemented. Even further, the method 300 may be implemented with the system 200 of FIG. 2, a different system, or a combination thereof.

At 302, image processing unit 206 receives the original MR image data. In some implementations, the image data is a three-dimensional medical image dataset. The MR image data may represent the whole patient's body, or portion thereof. The image data may be received from, for example, an imaging device 202, a storage device, a database system or an archiving system, such as a picture archiving and communication (PACS) system.

At 304, image processing unit 206 automatically localizes at least one anatomical structure of interest in the image data. The anatomical structure of interest may be, for example, a bone structure such as a vertebrae, rib, femur, skull, etc. It should be appreciated that the structure of interest may be any other types of anatomical structures.

In some implementations, the structure of interest is localized by performing a segmentation technique that generates a segmentation mask that delineates the anatomical structure of interest. The segmentation technique automatically finds voxels that belong to the particular anatomical structure of interest. The segmentation technique may include, but is not limited to, atlas-based segmentation, deformable model-based segmentation, classification-based tissue labeling, etc.

Alternatively, the structure of interest may be localized by detecting key landmarks associated with the structure of interest. A landmark (or semantic point) is any easily distinguishable or anatomically meaningful point on an image. For example, a landmark can represent an apex point where the outline is convex or concave. The detection method may include, but is not limited to, learning-based detection, salient point detection, etc.

At 306, image processing unit 206 highlights the localized structure of interest by reformatting the image data. The structure of interest is highlighted to advantageously increase the efficiency of reading the image data. The structure of interest may be highlighted by, for example, removing structures outside the segmentation mask so that only the structure of interest remains in the image data. Alternatively, the image data may be reformatted such that the structure of interest appears in fewer slices for compact reading.

More particularly, in some implementations, image processing unit 206 reformats the image data by applying the segmentation mask to the original image data to remove structures outside the mask. Accordingly, based on the segmentation mask, anatomical structures other than the structure under study may be removed or masked out to show only the structure of interest. Different MR contrast images and/or images from other modalities may be registered with the segmentation mask to apply the mask accordingly and allow for fusion and multi-modality reading. Rigid (e.g., linear transformation) or deformable (e.g., similarity measure) registration may be performed to align the mask with the images. Such registration may be performed manually, semi-automatically or automatically. Alternatively, such registration may be inherently performed during the imaging process, which allows the segmentation mask to be applied directly to the different contrast images without performing a registration algorithm.

Figure 4:
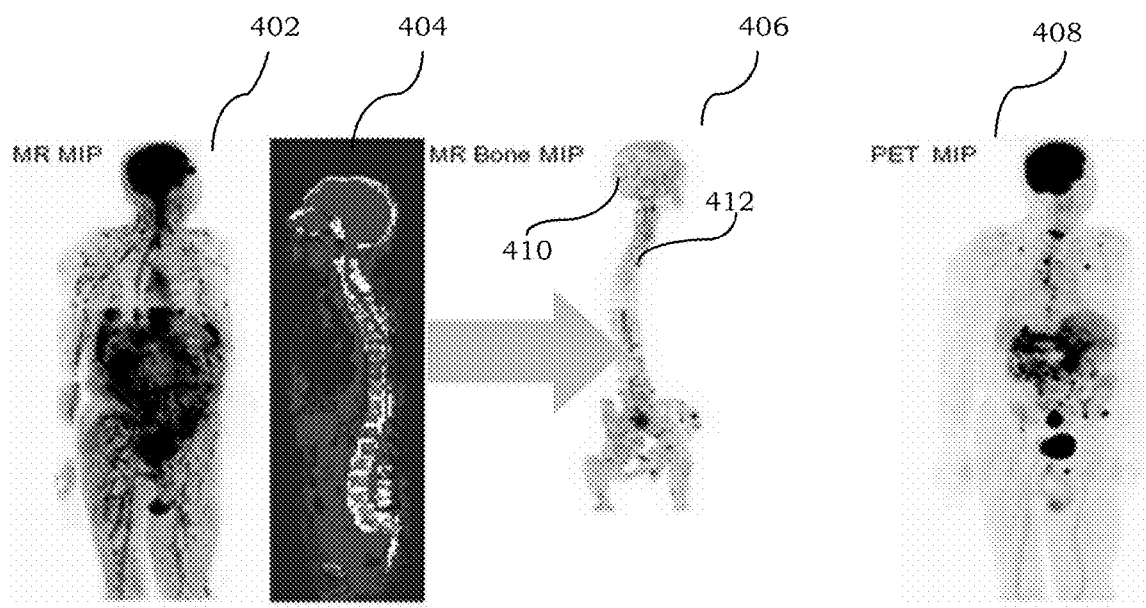
FIG. 4 shows exemplary images of a patient's body.

FIG. 4 shows exemplary images of a patient's body. More particularly, a coronal MR image 402 and a sagittal MR image 404 are extracted from the original image dataset. The original MR images 402-404 are reformatted to show only the bone structure of interest or skeleton 410. The reformatted 3D volume with only skeleton is rendered as a rotating maximum/minimum projection (MIP) image 406. Compared to the original MR MIP image 402, the suspicious bone metastases 412 are much more distinctive. This finding is also in accordance to the finding in the MIP image 408 of the standardized uptake value (SUV) PET.

In other implementations, image processing unit 206 reformats the image data by mapping detected landmarks of the structure of interest to a shape and warping the original image data by extrapolating displacements of the mapped landmarks throughout the image data. The shape may be a simple two-dimensional or three-dimensional geometric shape, such as a line or a plane. Each landmark on the structure of interest may be mapped to a corresponding point along the shape, resulting in a deformed structure (e.g., flattened spinal column).

One way to extrapolate the displacements of the mapped landmarks is through diffeomorphic extrapolation, which advantageously warps the image data while minimizing the distortion of surrounding tissues. An exemplary diffeomorphic extrapolation method is described in Twining, Carole J., Stephen Marsland, and Christopher J. Taylor, "Measuring Geodesic Distances on the Space of Bounded Diffeomorphisms," *BMVC*. Vol. 2. 2002, which is herein incorporated by reference. In the reformatted image data, the bone structures of interest appear in fewer number of slices than the original image data. This allows the structure of interest to be presented in a more concise visualization for quick analysis by the user. The one-to-one correspondence may be preserved to allow the user to refer back to the original image for validation if desired.

Figure 5:
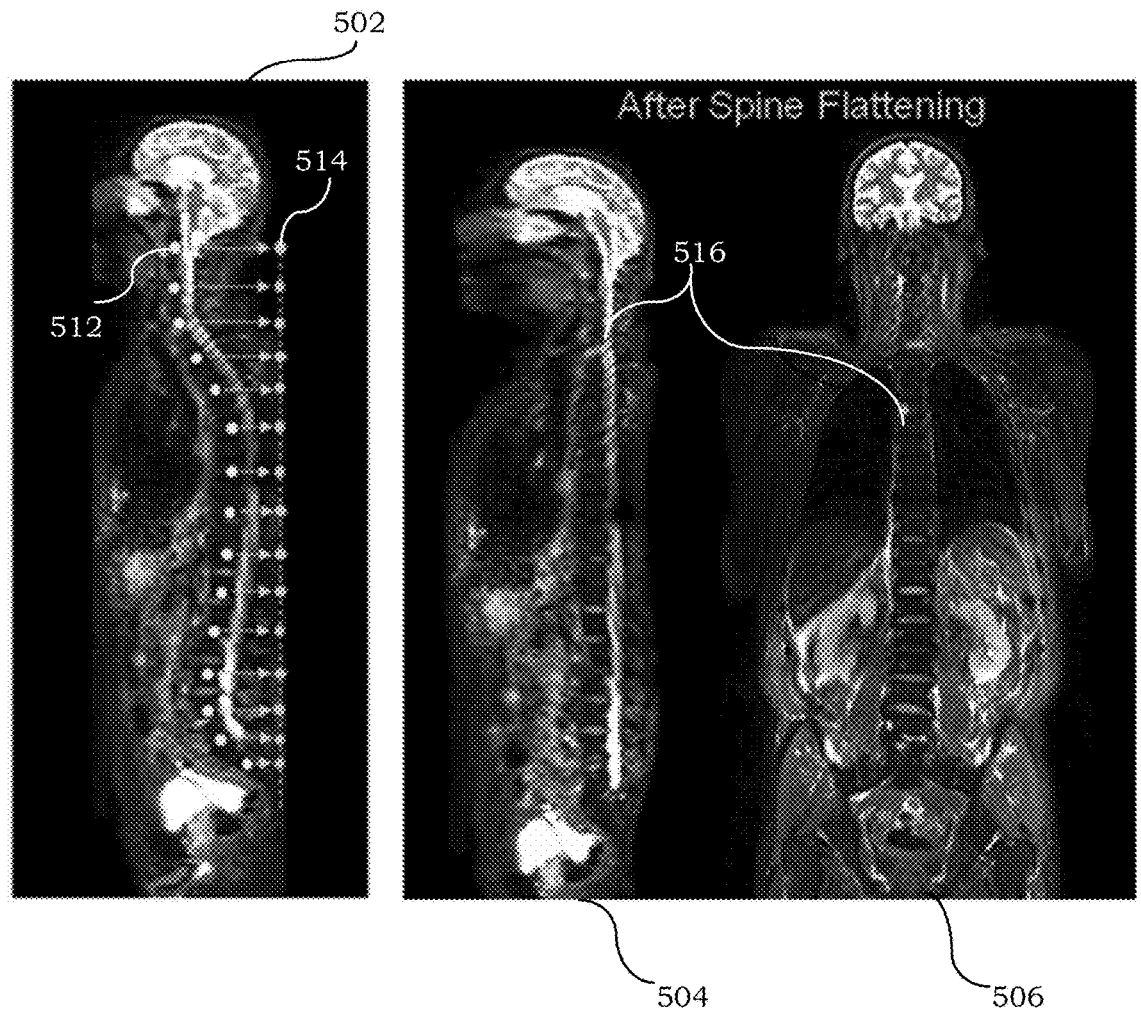
FIG. 5 illustrates exemplary flattening of the spinal column in image data.

FIG. 5 illustrates the flattening of the spinal column in the image data. A sagittal slice 502 of an MR image of the spine prior to spine flattening is shown. Here, the vertebrae centers 512 are detected and mapped to corresponding points 514 along a straight line. Diffeomorphic extrapolation is then performed to warp the MR image data. Sagittal and coronal slices (504 and 506) of the warped image data are shown. All vertebrae of the flattened spine 516 are now visible in the same coronal slice 506. Accordingly, radiologists can look for bone metastases by going through much fewer coronal slices.

In other implementations, image processing unit 206 reformats the image data by estimating the shape of the structure of interest based on the detected landmarks and mapping voxels on the shape to corresponding points on a visualization plane. The shape may be a three-dimensional geometric shape, such as an ellipse cylinder, triangle cylinder, circle cylinder, square, etc. The image data may be reformatted by resampling voxels on the shape from the original image data and displaying them on the visualization plane.

Figure 6A:
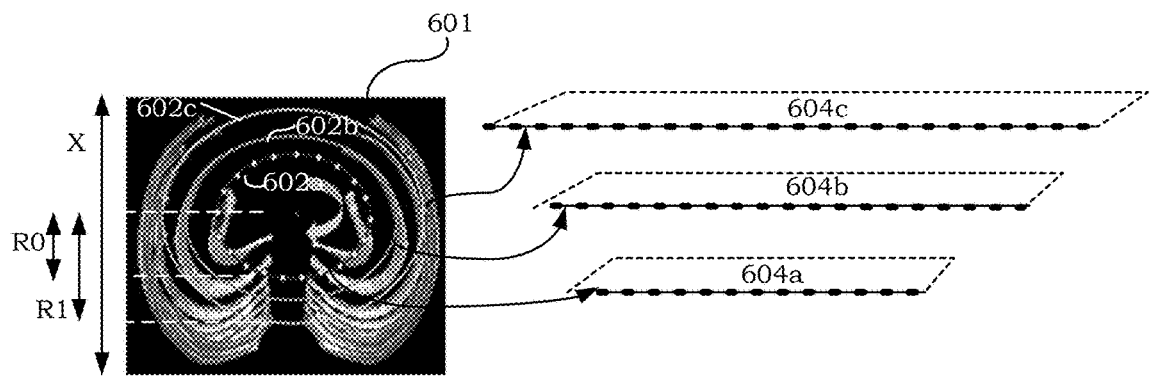
FIG. 6a shows exemplary mapping of voxels.

FIG. 6a shows an exemplary mapping of voxels. More particularly, a transverse slice 601 of the original image data of a rib cage is shown. The shapes of the rib cages are approximated by ellipse cylinders 602a-c. Voxels on each ellipse cylinder 602a-c may be mapped to a corresponding visualization plane 604a-c, resulting in roughly flattened (or unwrapped) coronal rib-cage visualizations, such as those shown in FIG. 6b.

Figure 6B:
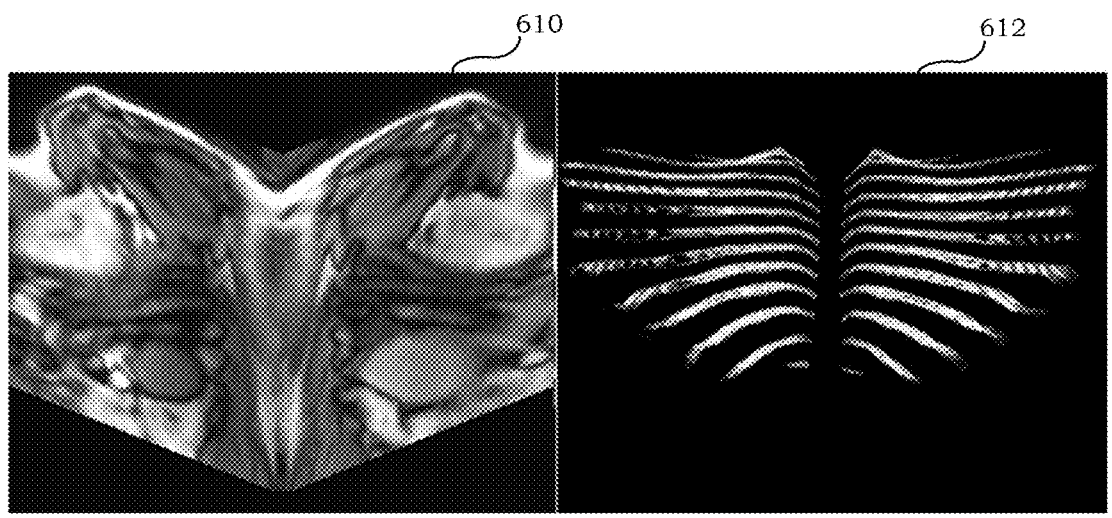
FIG. 6b shows an exemplary coronal multiplanar reconstruction (MPR) image and a coronal Volume Rendering Technique (VRT) image of flattened rib cages.

FIG. 6b shows a coronal multiplanar reconstruction (MPR) image 610 and a coronal Volume Rendering Technique (VRT) image 612 of the flattened rib cages. In the flattened images (610 and 612), each rib can be reviewed in just several coronal images or slices. Such visualization advantageously provides a more efficient way for browsing through the ribs.

In conventional techniques, a rib is traced and reviewed across the entire field of view. More particularly, the total number of coronal slices typically required to be read is proportional to the total number (X) of horizontal rows of voxels in transverse image 601. Compared to such techniques, this exemplary framework advantageously improves reading efficiency by reducing the number of slices that need to be reviewed. The reduced number of visualization slices (A) that are required may be determined by the following exemplary equation:

$$A = \frac{R1 - R0}{\text{Thickness of slice}} \quad (1)$$

wherein R1 is the radius of the largest ellipse and R0 is the radius of the smallest ellipse.

Rib flattening algorithms have been designed for CT images. Such algorithms achieved flattening by tracing the rib center lines. The flattened rib view helps to improve the reading efficiency of CT images. While the concept is also applicable to MR images, it is technically difficult to trace ribs in MR images due to the low MR signal in cortical bones and large slice thickness. In the present framework, rib cages are estimated by ellipse cylinders or other suitable shapes. The centers, orientations and sizes of these cylinders can be estimated by a few anatomical landmarks that are visible in the MR imaging modality. Compared to the rib tracing-based rib flattening techniques, the present framework is advantageously applicable in more imaging modalities.

Returning to FIG. 3, at 308, image processing unit 206 renders the reformatted image data for display to a user. Different rendering methods, including multi-planar reformatting (MPR), maximum/minimum projection images (MIP) and Volume Rendering Technique (VRT) may be applied on the reformatted image data with the highlighted structure of interest. The rendered image data may be displayed at, for example, output device 208 or workstation 203. The user may easily read the displayed image data to detect, for example, bone metastases or other abnormalities. In some implementations, the original image data received at 302 is displayed along with the rendered image data. A point-to-point correspondence between the two sets of image data may be presented to allow the user to verify detection results by referring back to the original image data.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A computer-implemented method of visualization, comprising:
    (i) receiving magnetic resonance image data;
    (ii) automatically localizing at least one bone structure of interest in the image data that appears only in a first number of slices in the image data;
    (iii) highlighting and flattening the localized bone structure of interest by reformatting the image data into reformatted image data by
        estimating a cylindrical shape of the localized bone structure of interest based on landmarks associated with the localized bone structure of interest,
        resampling voxels on a surface of the cylindrical shape from the image data, and
        mapping the resampled voxels on the cylindrical shape to corresponding points on a visualization plane to flatten the localized bone structure of interest, and
        wherein the bone structure of interest appears only in a second number of slices of the reformatted image data, wherein the second number of slices is less than the first number of slices; and
    (iv) rendering the reformatted image data for display via a display device.

2. The method of claim 1 wherein automatically localizing the bone structure of interest comprises performing a segmentation technique and generating a segmentation mask that delineates the bone structure of interest.

3. The method of claim 2 wherein the segmentation technique comprises atlas-based segmentation, deformable model-based segmentation, classification-based tissue labeling, or a combination thereof.

4. The method of claim 2 wherein highlighting the localized bone structure of interest comprises applying the segmentation mask to the image data and removing structures outside the mask.

5. The method of claim 1 wherein automatically localizing the bone structure of interest comprises detecting the landmarks associated with the localized bone structure of interest.

6. The method of claim 5 wherein detecting the landmarks associated with the localized bone structure of interest comprises performing learning-based detection, salient point detection, or a combination thereof.

7. The method of claim 1 wherein highlighting and flattening the localized bone structure of interest comprises estimating multiple cylindrical shapes of the bone structure of interest based on the landmarks associated with the localized bone structure of interest and mapping voxels on the multiple cylindrical shapes to corresponding visualization planes.

8. The method of claim 1 wherein the cylindrical shape comprises an ellipse cylinder or a circle cylinder.

9. The method of claim 1 wherein rendering the reformatted image data for display via the display device comprises performing multi-planar reformatting (MPR), maximum/minimum intensity projection (MIP) and Volume Rendering Technique (VRT) based on the reformatted image data.

10. A non-transitory computer readable medium embodying a program of instructions executable by machine to perform steps for visualization, the steps comprising:

(i) receiving magnetic resonance image data;
(ii) automatically localizing at least one bone structure of interest in the image data that appears only in a first number of slices in the image data;
(iii) highlighting and flattening the localized bone structure of interest by reformatting the image data into reformatted image data by
  estimating a cylindrical shape of the localized bone structure of interest based on landmarks associated with the localized bone structure of interest,
  resampling voxels on a surface of the cylindrical shape from the image data,
  mapping the resampled voxels on the cylindrical shape to corresponding points on a visualization plane to flatten the localized bone structure of interest, and
  wherein the bone structure of interest appears only in a second number of slices of the reformatted image data, wherein the second number of slices is less than the first number of slices; and
(iv) rendering the reformatted image data for display via a display device.

* * * * *